United States Patent [19] [11] 4,154,691
Mauric et al. [45] May 15, 1979

[54] FLAMEPROOFING DISPERSIONS CONTAINING PHOSPHORIC ACID DERIVATIVES

[75] Inventors: Claudine Mauric, Basel; Rainer Wolf, Allschwil, both of Switzerland

[73] Assignee: Sandoz Ltd., Basel, Switzerland

[21] Appl. No.: 832,177

[22] Filed: Sep. 12, 1977

Related U.S. Application Data

[62] Division of Ser. No. 689,970, May 26, 1976, Pat. No. 4,062,687.

[51] Int. Cl.$^2$ ................................................ C09K 3/28
[52] U.S. Cl. .................................. 252/8.1; 106/15.05; 428/921
[58] Field of Search ................... 252/8.1; 106/15 FP; 428/921

[56] References Cited

U.S. PATENT DOCUMENTS

| 4,020,262 | 4/1977 | LeBlanc et al. | 252/8.1 X |
| 4,026,808 | 5/1977 | Duffy | 252/8.1 |

*Primary Examiner*—Stephen J. Lechert, Jr.
*Attorney, Agent, or Firm*—Gerald D. Sharkin; Richard E. Vila; Joseph J. Borovian

[57] ABSTRACT

Flameproofed cellulose includes as a flameproofing agent a compound selected from esters, ester-amides and amides of pyrophosphoric, of mono-, di- and trithiopyrophosphoric, of triphosphoric, and of mono-, di-, tri- and pentathiotriphosphoric acids.

10 Claims, No Drawings

FLAMEPROOFING DISPERSIONS CONTAINING PHOSPHORIC ACID DERIVATIVES

This is a division of application Ser. No. 689,970 filed May 26, 1976, now issued as U.S. Pat. No. 4,062,687.

The present invention relates to flameproofed polymeric organic materials.

In particular, the present invention provides flameproofed cellulose, preferably regenerated cellulose, including as a flameproofing agent a compound selected from esters, ester-amides and amides of pyrophosphoric, of mono-, di- and trithiopyrophosphoric, of triphosphoric, and of mono-, di-, tri- and pentathiotriphosphoric acids.

The preferred flameproofed cellulose according to the present invention includes a flameproofing agent a compound of formula I,

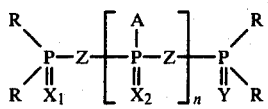

in which each R, independently, is a radical $-OR_1$ (a) or

or two moieties R bound to the same phosphorus atom form a radical (c),

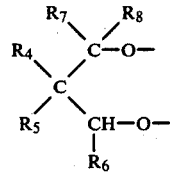

and each of the other two moieties R, independently, is a radical (a) or (b), or the other two moieties R bound to the same phosphorus atom form a second radical (c), independent from the first radical (c), each of $X_1$, $X_2$, Y and Z, independently, is oxygen or sulphur, n is zero or 1, A is a radical (a)

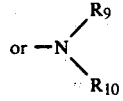

each $R_1$, independently, is methyl; ethyl or propenyl, each unsubstituted or substituted with up to 3 halogen atoms or with a $(C_{1-6})$alkoxy radical; $(C_{3-12})$alkyl or $(C_{4-12})$alkenyl, each unsubstituted or substituted with up to 4 halogen atoms; $(C_{5-8})$cycloalkyl or $(C_{5-8})$cycloalkyl$(C_{1-4})$alkyl, containing 7-9 carbon atoms in toto, each unsubstituted or substituted with 1 or 2 halogen atoms; or phenyl or phenyl-$(C_{1-4})$alkyl, each unsubstituted or substituted aromatically with up to 5 halogen atoms or with up to 3 $(C_{1-3})$alkyl and/or $(C_{1-3})$alkoxy radicals, each $R_2$, independently, is $(C_{1-4})$alkyl, cyclohexyl or benzyl; or phenyl, unsubstituted or substituted with 1 or 2 chlorine atoms of which only one can occupy an ortho-position, with a bromine atom in the para-position, or with up to 2 $(C_{1-3})$alkyl and/or $(C_{1-3})$ alkoxy radicals, the aggregate of the carbon atoms thereof not exceeding 3, each $R_3$, independently, is $(C_{1-4})$alkyl or hydrogen, or any $R_2$ and $R_3$, independently, together with the nitrogen atom to which they are bound, form a 5- or 6-membered, saturated heterocyclic ring which may contain as a ring member an oxygen or sulphur atom, or a second nitrogen atom to which is bound a $(C_{1-4})$alkyl radical, each $R_4$ and $R_5$, independently, is hydrogen, $(C_{1-4})$alkyl, $CH_2Cl$, $CH_2Br$ or phenyl, or any $R_4$ and $R_5$, independently, together with the carbon atom to which they are bound, form a cyclohexylidene, cyclohexenylidene or 3,4-dibromocyclohexylidene ring, each $R_6$ and $R_8$, independently, is hydrogen or $(C_{1-4})$alkyl, each $R_7$, independently, is hydrogen or methyl, $R_9$ is methyl; ethyl, unsubstituted or substituted with a halogen atom; propyl, unsubstituted or substituted with 1 or 2 halogen atoms; $(C_{4-12})$alkyl, unsubstituted or substituted with up to 3 halogen atoms; cyclohexyl; benzyl; or phenyl, unsubstituted or substituted with 1 or 2 chlorine atoms, or with a bromine atom in the para-position, and/or in both cases with up to 2 $(C_{1-3})$alkyl and/or $(C_{1-3})$alkoxy radicals, the aggregate of the carbon atoms thereof not exceeding 3, $R_{10}$ is hydrogen; methyl; ethyl, unsubstituted or substituted with a halogen atom; propyl, unsubstituted or substituted with up to 2 halogen atoms; $(C_{4-12})$alkyl, unsubstituted or substituted with up to 3 halogen atoms; cyclohexyl; benzyl; or phenyl, or $R_9$ and $R_{10}$, together with the nitrogen atom to which they are bound, form a 5- or 6-membered, saturated heterocyclic ring which may contain as a ring member an oxygen or sulphur atom, or a second nitrogen atom, to which is bound a $(C_{1-4})$alkyl radical, with the provisos:
(i) when one or more of $X_1$, $X_2$ and Y is oxygen, then Z can only be oxygen,
(ii) when $X_1$ and Y are both oxygen, then up to 2 only of the moieties R can be a radical (a),
(iii) when there are more than 2 radicals (a) in the molecule, up to 2 of them only can be methoxy,
(iv) when Z is oxygen and n is zero, only one radical (c) can be present in the molecule,
(v) when $X_1$ or Y is oxygen, then $R_2$ in any radical (b) attached to that same phosphorus atom as the oxygen atom is other than alkyl,
(vi) when two radicals (b) are attached to a phosphorus atom and $X_1$ or Y attached to that same phosphorus atom is sulphur, then both of the moieties $R_2$ in these radicals (b) are $(C_{1-4})$alkyl,
(vii) when n is 1, or when n is zero and $R_2$ in any radical (b) is $(C_{1-4})$alkyl, any $R_3$, or $R_3$ in that same radical (b), respectively, is other than hydrogen,
(viii) at least one of $R_4$, $R_5$, $R_6$, $R_7$ and $R_8$ in any radical (c) is other than hydrogen,
(ix) when each of $R_4$ and $R_5$, independently, in any radical (c) is $CH_2Cl$ or $CH_2Br$ or both $R_4$ and $R_5$, together with the carbon atom to which they are bound form one of the rings indicated above, each of $R_6$, $R_7$ and $R_8$ in the same radical (c) is hydrogen, and (x) when each of $X_1$ and Y is oxygen, each of $R_4$ and $R_5$, independently, in any radical (c) is $CH_2Cl$ or $CH_2Br$ or both $R_4$ and $R_5$, together with the carbon atom to which they are bound, form one of the rings indicated above.

In the above definition of formula I, it is to be understood that any alkyl radical signified by $R_1$, $R_2$, $R_3$, $R_5$, $R_6$, $R_8$, $R_9$ and $R_{10}$, and any alkyl substituent, may be straight or branched chain when containing 3 or more carbon atoms, and that the term "halogen" embraces chlorine and bromine.

When any moiety $R_1$ is unsubstituted or substituted alkyl, the alkyl radical preferably contains 2 to 6 carbon atoms, and an ethyl radical, when substituted, preferably bears a single chlorine or bromine atom, and a $(C_{3-6})$alkyl radical, when substituted, preferably up to 3 halogen atoms. Depending on the significances of $X_1$, Y, Z and n, any $R_1$ has certain more preferred significances of unsubstituted or substituted alkyl. Thus when $X_1$ and Y are both sulphur, Z is oxygen and n is zero, $R_1$, when alkyl, is more preferably n-propyl or isopropyl, unsubstituted or substituted with 1 or 2 halogen atoms, or $(C_{4-6})$alkyl, preferably unsubstituted or substituted with up to 3 halogen atoms. When $X_1$, Y and Z are each sulphur and n is zero, $R_1$, when alkyl, is more preferably unsubstituted propyl or butyl, and when $X_1$ and Y are each sulphur, Z is oxygen and n is 1, n- or isopropyl, unsubstituted or substituted with up to 2 halogen atoms, or unsubstituted $(C_{4-6})$ alkyl.

When any moiety $R_1$ is unsubstituted or substituted alkenyl, the alkenyl radical preferably contains 3 to 6 carbon atoms. When substituted, it preferably bears up to 2 halogen atoms. The preferred cycloalkyl radical signified by any $R_1$ moiety, is cyclohexyl, which is, more preferably, unsubstituted.

When any moiety $R_1$ is unsubstituted or substituted phenylalkyl, this is preferably benzyl, which when substituted preferably bears up to 3 chlorine atoms or a single bromine atom in the para-position on the phenyl nucleus.

When any moiety $R_1$ is substituted phenyl, the phenyl nucleus preferably bears up to 3 chlorine atoms or a single bromine atom in the para-position, or up to 3 alkyl radicals. Any such alkyl substituent preferably contains 1 to 3 carbon atoms, and more preferably is methyl, of which the most preferred substituent is a single methyl radical. Most preferably, $R_1$, when signifying unsubstituted or substituted phenyl, is unsubstituted phenyl or mono-methylphenyl.

Of the significances for $R_1$ given in the definition of formula I above, unsubstituted or substituted alkyl, alkenyl, cycloalkyl, phenylalkyl and phenyl are preferred, and unsubstituted or substituted alkyl is the most preferred. When more than 2 moieties $R_1$ are present, preferably no more tham two of them signify ethyl.

When any moiety $R_2$ is unsubstituted or substituted alkyl, the alkyl radical preferably contains 1 to 3 carbon atoms. Independently, any alkyl radical signified by $R_2$ or $R_3$ is preferably unsubstituted. When any moiety $R_2$ or $R_3$, independently, is substituted phenyl, the preferred substituent is a single chlorine or bromine atom, preferably in the para-position, or alkyl radical, of which the preferred alkyl is methyl.

If X or Y is oxygen and a radical (b) is attached to the same phosphorus atom as that moiety $X_1$ or Y, $R_2$ in the radical (b) is preferably unsubstituted or substituted phenyl. The preferred substituent is p-chloro or methyl, the latter preferably being in the ortho-position. More preferably, however, $R_2$ is unsubstituted or o-methyl-substituted phenyl. Furthermore, when either of $R_2$ or $R_3$ is ethyl or propyl, the other is preferably also ethyl or propyl, respectively.

When any moiety $R_3$ is alkyl, this preferably contains 1 to 3 carbon atoms, and when $X_1$, Y and Z are oxygen, n is zero and any R is a radical (b), $R_3$ therein is preferably hydrogen.

Of the significances for $R_2$ given in the definition of formula I above, alkyl and unsubstituted or substituted phenyl are preferred.

When either of the moieties $R_4$ and $R_5$, independently, is an alkyl radical, this preferably contains 1 to 3 carbon atoms, of which methyl is the preferred alkyl radical. Of the significances for either $R_4$ or $R_5$ given in the definition of formula I above, alkyl, $CH_2Cl$, $CH_2Br$ and the rings formed by $R_4$, $R_5$ and the carbon atom to which they are bound are preferred, and alkyl, $CH_2Cl$ and $CH_2Br$ are more preferred. If $R_4$ is $CH_2Br$, $R_5$ bound to the same carbon atom is preferably other than $CH_2Cl$, and vice versa. $CH_2Br$ is preferred to $CH_2Cl$, and $R_4$ and $R_5$ preferably have the same significances.

Each of $R_6$, $R_7$ and $R_8$, independently, is preferably hydrogen.

When any moiety $R_9$ or $R_{10}$ is unsubstituted or substituted alkyl, the alkyl radical preferably contains 1 to 4 carbon atoms, which more preferably is unsubstituted. When any moiety $R_9$ of $R_{10}$ is unsubstituted or substituted phenyl, this is preferably unsubstituted.

The preferred heterocyclic radicals formed by $R_9$, $R_{10}$ and the nitrogen atom to which they are bound are piperidino and morpholino, of which piperidino is more preferred.

On the same radical (d), $R_9$ and $R_{10}$ are preferably identical.

Of all the significances of $R_9$ given in the definition of formula I above, the preferred ones are unsubstituted or substituted alkyl, cyclohexyl and benzyl and, together with $R_{10}$ and the nitrogen atom to which both are bound, the 5- or 6-membered saturated heterocyclic ring. For $R_{10}$ the preferred significances are hydrogen and unsubstituted or substituted alkyl, and, together with $R_9$ and the nitrogen atom to which both are bound, the 5- or 6-membered saturated heterocyclic ring. More preferably, either of $R_9$ and $R_{10}$, independently, is unsubstituted or substituted alkyl or both, together with the nitrogen atom to which both are bound, the heterocyclic ring indicated above.

In general when $X_1$, Y and Z are oxygen and n is zero, each R, independently, is preferably a radical (b), and when $X_1$ and Y are sulphur, Z is oxygen or sulphur and n is zero, or, in the case when Z is oxygen, n is additionally 1, each R, independently, is preferably a radical (a) or two moieties R bound to the same phosphorus atom form a radical (c). In the case where $X_1$ and Y are sulphur, Z is oxygen and n is zero, more preferably each R, independently, is a radical (a), and in the cases where $X_1$ and Y are sulphur, and either Z is sulphur and n is zero or Z is oxygen and n is 1, more preferably two moieties R bound to the same phosphorus atom form a radical (c).

The preferred significance for $X_2$ is sulphur and for A a radical (d).

The flameproofed cellulose of the present invention more preferably includes as a flameproofing agent a compound of formula Ia,

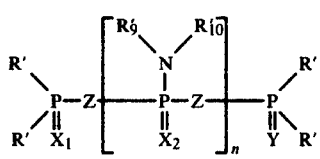

in which each R', independently, is a radical-OR$_1$' (a')

or two moieties R' bound to the same phosphorus atom form a radical (c')

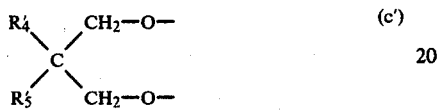

and each of the other two moieties R', independently, is a radical (a') or (b'), or the other two moieties R' bound to the same phosphorus atom form a second radical (c'), independent from the first radical (c'), each of X$_1$, X$_2$, Y and Z, independently, is oxygen or sulphur, n is zero or 1, each R$_1$', independently, is ethyl, unsubstituted or substituted with a halogen atom; (C$_{3-6}$)alkyl, unsubstituted or substituted with up to 3 halogen atoms; (C$_{3-6}$)alkenyl, unsubstituted or substituted with up to 2 halogen atoms; cyclohexyl; or phenyl or benzyl, each unsubstituted or substituted aromatically with up to 3 chlorine atoms or with a bromine atom in the para-position or, in the case of phenyl, with up to 3 methyl radicals, each R$_2$', independently, is (C$_{1-3}$)alkyl or phenyl, the latter unsubstituted or substituted with a chlorine atom, with a bromine atom in the para-position or with a methyl radical, each R$_3$', independently, is (C$_{1-3}$)alkyl or hydrogen, each R$_4$' and R$_5$', independently, is (C$_{1-4}$)alkyl, CH$_2$Cl or CH$_2$Br, or any R$_4$' and R$_5$', independently, together with the carbon atom to which they are bound, form a cyclohexylidene, cyclohexenylidene or 3,4-dibromocyclohexylidene ring, R$_9$' is (C$_{1-4}$)alkyl, cyclohexyl, benzyl or phenyl, R$_{10}$' is hydrogen, (C$_{1-4}$)alkyl, cyclohexyl, benzyl or phenyl, or R$_9$' and R$_{10}$', together with the nitrogen atom to which they are bound, form a piperidino or morpholino radical, with the provisos:

(i) when one or more of X$_1$, X$_2$ and Y is oxygen, then Z can only be oxygen, (ii) when X$_1$ and Y are both oxygen, then each moiety R', independently, is a radical (b'), (iii) when Z is oxygen and n is zero, only one radical (c') can be present in the molecule, (iv) when X$_1$ or Y is oxygen, then R$_2$' in any radical (b') bound to that same phosphorus atom as the oxygen atom is other than alkyl, (v) when two radicals (b') are attached to a phosphorus atom, and X$_1$ or Y attached to that same phosphorus atom is sulphur, then both of the moieties R$_2$ in these radicals (b') are (C$_{1-3}$)alkyl, (vi) when one of the moieties R$_2$' and R$_3$' bound to the same nitrogen atom in a radical (b') is ethyl or propyl, the other cannot be other than ethyl or propyl, (vii) when n is 1, or when n is zero and R$_2$' in any radical (b') is (C$_{1-3}$)alkyl, any R$_3$', or R$_3$' in that same radical (b'), respectively, is other than hydrogen, and (viii) when each of X$_1$ and Y is oxygen, each of R$_4$' and R$_5$', independently, in any radical (c') is CH$_2$Cl or CH$_2$Br or both R$_4$' and R$_5$', together with the carbon atom to which they are bound form one of the rings indicated above.

The flameproofed cellulose of the present invention most preferably includes as a flameproofing agent a compound of one of the formulae Iaa, Iab, Iac and Iad following:

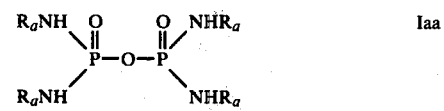

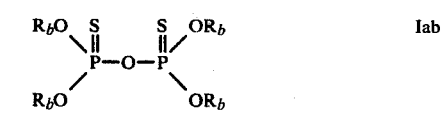

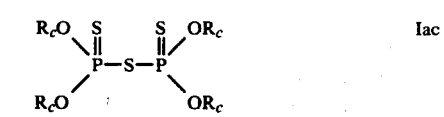

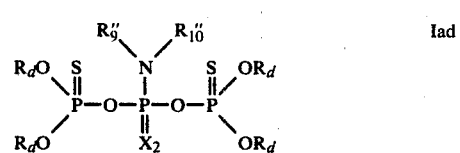

in which R$_a$ is phenyl, unsubstituted or substituted with a chlorine atom in the para-position or with a methyl radical, each R$_b$, independently, is n-propyl or isopropyl, each unsubstituted or substituted with 1 or 2 halogen atoms; (C$_{4-6}$) alkyl, unsubstituted or substituted with up to 3 halogen atoms; cyclohexyl; or phenyl, unsubstituted or substituted with a methyl radical; or two moieties R$_b$ bound via oxygen atoms to the same phosphorus atom form a radical (c''),

wherein each R$_4$'' and R$_5$'', independently, is (C$_{1-3}$) alkyl, CH$_2$Cl or CH$_2$Br, with the proviso that when R$_4$'' is CH$_2$Br, R$_5$'' is other than CH$_2$Cl, and when R$_5$'' is CH$_2$Br, R$_4$'' is other than CH$_2$Cl, with the proviso that no more than one radical (c'') is present in the molecule, R$_c$ is propyl or butyl, or two moieties R$_c$ bound via oxygen atoms to the same phosphorus atom form a radical (c'') as defined above, R$_d$ is n-propyl or isopropyl each unsubstituted or substituted with 1 or 2 halogen atoms; (C$_{4-6}$) alkyl; or 2 moieties R$_d$ bound via oxygen atoms to the same phosphorus atom form a radical (c″), as defined above, $X_2$ is oxygen or sulphur, $R_9''$ is $(C_{1-4})$ alkyl, cyclohexyl or benzyl, and $R_{10}''$ is hydrogen or $(C_{1-4})$ alkyl, or $R_9''$ and $R_{10}''$, together with the nitrogen atom to which they are bound, form a piperidino or morpholino ring.

Preferably the flameproofed cellulose of the present invention including a compound of formula I as a flameproofing agent is flameproofed regenerated cellulose.

The compounds of formula I′,

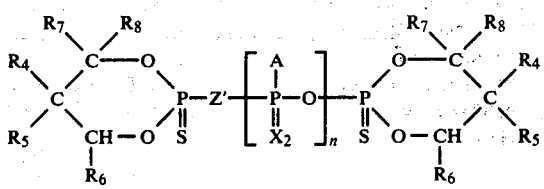

in which $X_2$, n, A and each of the $R_4$'s, $R_5$'s, $R_6$'s, $R_7$'s and $R_8$'s are as defined above, and, when n is zero, Z′ is sulphur and at least one of the $R_4$ and $R_5$ moieties is other than methyl, and, when n is 1, Z′ is oxygen, are new, and are also provided by the present invention.

The present invention further provides a process for the production of a compound of formula I′, as defined above, which comprises (a), in the case when n is zero, and Z′ is sulphur, eliminating hydrogen and sulphur simultaneously or first hydrogen and then sulphur from a compound or mixture of two compounds of formula II,

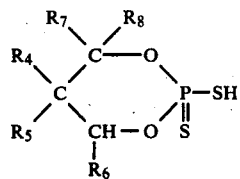

in which $R_4$, $R_5$, $R_6$, $R_7$ and $R_8$ are as defined above, or (b), in the case when n is 1 and Z′ is oxygen, reacting a compound or mixture of two compounds of formula III,

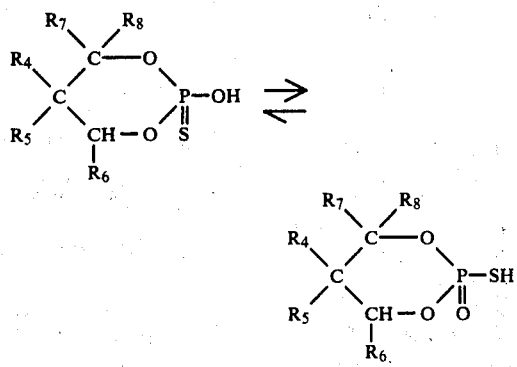

in which $R_4$, $R_5$, $R_6$, $R_7$ and $R_8$ are as defined above, with a compound of formula IV,

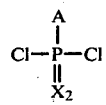

in which $X_2$ and A are as defined above, in a molar ratio of the compound or mixture of compounds of formula III:compound of formula IV of 2:1.

It is to be understood that when one compound of formula II is used in variant (a) above, the product is structurally symmetrical.

In the case of the production of compounds of formula I′ in which n is zero and Z′ is sulphur according to variant (a) above, the process conditions are known from analogous processes involving the same reaction principle. For the elimination of hydrogen an example of a suitable agent is iodine, and for that of sulphur, an example thereof is triphenylphosphine.

Similarly, the process conditions for the production of compounds of formula I′ in which n is 1 and Z′ is oxygen according to variant (b) above are known from analogous processes involving the same reaction principle. Preferably the reaction is conducted in the presence of an acid-binding agent, especially a tertiary amine or a heterocyclic compound of aromatic nature containing a ring nitrogen atom, e.g. pyridine.

The intermediates of formulae II, III and IV above may be produced in conventional manner from known starting materials or from starting materials produced by analogous processes to those for producing the known starting materials.

The compounds of formula II and III are new, and are also provided by the present invention.

The present invention further provides a method of producing flameproofed regenerated cellulose comprising regenerating cellulose from its solution e.g. viscose, containing a flameproofing-effective amount of a flameproofing agent, as indicated above. Thus the regenerated cellulose produced has the agent incorporated therein and is flameproofed by virtue of its presence.

The term "regenerated cellulose" is well understood in the art to which it pertains. Amongst the procedures for producing regenerated cellulose are those involving the formation at one stage of alkali cellulose xanthate or a tetramine cupric hydroxide complex of cellulose, and such procedures are so adapted according to this embodiment of the method to include the regeneration of cellulose from its solution containing the flameproofing agent, as indicated above.

Prior to the regeneration, cellulose is brought into solution, e.g. by such known processes as converting it into a soluble derivative by the xanthate method or through formation of the tetramine cupric hydroxide complex thereof. The flameproofing agent is then added to the cellulose solution, for example by itself or as a fine dispersion in water. When added alone, the agent may be introduced into the cellulose solution either continuously or discontinuously, i.e. in batches, and thereafter vigorous stirring of the cellulose solution containing the compound may be applied to distribute it uniformly in the solution. The same technique may also be adopted for the addition of an aqueous dispersion of the agent. Preferably the weight of compound of formula I present in the cellulose solution from which flameproofed regenerated cellulose is to be produced is in the range 5 to 35% of the weight of the cellulose starting material, e.g. α-cellulose, or more preferably 8 to 25% of its weight. In all cases it can be advantageous to add conventional dispersion stabilisers and/or dispersion agents to the cellulose medium to promote uniformity of distribution of the compound in the cellulose solution.

Other flameproofing compounds, e.g. reaction products of a phosphorus nitrile chloride with glycols e.g. neopentylglycol, cyclodiphosphazanes or thionocyclodiphosphazanes, e.g. 2,4-dianilino-2,4-dioxo-1,3-diphenylcyclodiphosphazanes, may be added to the cellulose solution as well as a compound of formula I. In particular, 2,4-dianilino-1,3-cyclodiphosphazane is preferably added to the cellulose solution together with a compound of formula I.

Such other flameproofing compounds may be added with the compound of formula I as a fine dispersion in water.

The amount of such additional flameproofing agents when employed may be up to 90% by weight of the total flameproofing agent present in the cellulose solution. In the case of reaction products of a phosphorus nitrile chloride and a glycol, a cyclodiphosphazane and a thionocyclodiphosphazane, such auxiliary flameproofing agent preferably constitutes 10 to 70%, or more preferably 15 to 60%, of the total weight of flameproofing agent in the solution.

The regenerated cellulose is produced in shaped form from the solution in conventional manner by forcing the solution into a precipitation bath through fine nozzles or slots, thereby producing filaments or sheets, respectively. Apart from flame resistance, the so-produced flameproofed regenerated cellulose possesses its normal technically important properties which are only slightly affected by the presence of the incorporated flameproofing agent.

The compounds of formula I, as defined above, are also useful for the flameproof treatment of polymeric organic materials besides cellulose, and the present invention further provides a flameproofed polymeric organic material, other than cellulose, including as a flameproofing agent a compound of formula I, as defined above.

In the flameproofed polymeric organic materials of the present invention, preferred polymeric organic materials, other than cellulose, rendered flameproofed by the inclusion of a compound of formula I are polyolefins, e.g. polyethylene and polypropylene, polyesters, polyacrylic esters, e.g. polymethyl methacrylates, polyphenylene oxides, polyurethanes, polystyrene, polyamides, e.g. nylon, polypropylene oxide, polyacrylonitrile, copolymers of the aforementioned polymers, acrylonitrile-butadiene-styrene (ABS) terpolymers and natural fibrous materials, other than cellulose. For the flameproofing of these polymeric organic materials except regenerated cellulose and natural fibrous materials those flameproofing agents which contain one or more halogen substituents are most suitable. Most preferably, the polymeric organic material rendered flameproof by the inclusion therein of a compound of formula I is regenerated cellulose.

The present invention further provides a method of producing a flameproofed polymeric organic material, other than cellulose, comprising treating the polymeric organic material, directly or indirectly, with a flameproofing-effective amount of a compound of formula I, as defined above. Suitable polymeric organic materials which are flameproofed according to this method of the present invention include the specific ones mentioned above.

In this specification, by the term "treating" is meant either incorporating into the body of the polymeric organic material or surface coating such material, depending on the substrate to be flameproofed.

This method may be carried out in a manner known per se, of which the following two embodiments, which relate to the production of flameproofed polymeric organic materials other than regenerated cellulose and natural fibrous materials, are examples:

In one embodiment, the flameproofing agent is mixed with the appropriate monomer(s) and/or prepolymer, whereafter polymerisation or copolymerisation, e.g. by polycondensation and/or polyaddition, is effected. The resulting product, which has the compound distributed therethrough, may then be extruded, injection moulded or otherwise formed into final shape. This embodiment is particularly suitable for producing flameproofed polyurethanes and polyolefins, and illustrates the indirect incorporation of the agent in the organic material.

In a second embodiment, the flameproofing agent is mixed with the polymeric organic material in molten or dissolved form, after which the flameproofed material may be converted into the desired final shape, e.g. by extrusion into, inter alia, films, injection moulding or spinning to produce fibres. This embodiment is particularly suitable for producing flameproofed polypropylene and polyacrylonitrile, and provides an illustration of the direct incorporation of the flameproofing agent into the polymeric organic material.

The amount of flameproofing compound of formula I suitably incorporated into the polymeric organic materials, other than regenerated cellulose and natural fibrous materials for imparting satisfactory flameproofing properties thereto will naturally depend on several factors, including the particular compound of formula I employed, the nature of the organic material to be flameproofed and the mode of incorporation. However, satisfactory results are generally obtained when the amount of compound employed is in the range 1 to 40%, preferably 2 to 10%, and more preferably 2 to 6%, of the weight of the polymeric organic material to be flameproofed.

Natural fibrous materials, including natural cellulose, e.g. cotton, are treated, according to the method of the present invention, by coating the flameproofing agent suitably present in a coating liquor, e.g. a solution or aqueous dispersion, onto the substrate. Thus the material is treated directly with the flameproofing agent. Where blend fabrics of synthetic and/or semi-synthetic and natural fibrous organic materials e.g. polyester-cotton blend fabrics, are to be flameproofed, the synthetic or semi-synthetic organic material may be independently treated according to the method of the invention, e.g. as described in the above embodiments, and then blended with the optionally flameproof-treated natural fibrous organic material, the blend fabric then being optionally further treated with a compound of formula I by coating if a higher degree of flameproofing is necessary or desired. Alternatively, the untreated blend fabric may be treated with the compound by coating.

The present invention is illustrated by the following Examples, in which the parts and percentages are by weight.

EXAMPLE 1

A suspension of 44.4 parts of diphosphorus pentasulphide and 104.5 parts of 2,2-dibromomethyl-1,3-propanediol in 200 parts of toluene is warmed to 90° C. over a period of 2½ hours. The reaction is continued at this temperature for 7 hours, after which the mixture is heated for a further 2 hours under reflux. A clear solution results, from which the solvent is removed by evaporation. The residue is crystallised from carbon tetrachloride, yielding a solid with a m.p. 117°-120° C.

64 Parts of the solid product obtained as above are suspended in 250 parts of water and 12.2 parts of a 25% ammonia solution. To the suspension is added, over a period of 6 hours, a solution of 22.65 parts of iodine and 44.95 parts of a potassium iodide in 178.8 parts of water. The mixture is stirred at room temperature for a further hour.

The precipitate obtained is collected by filtration, dried and suspended in 150 parts of benzene. To this suspension at 30° C. is added dropwise a solution of 14 parts of triphenylphosphine in 60 parts of benzene during a period of 20 minutes, and the mixture is maintained at 30° C. for a further 8 hours. Thereafter the benzene solvent is removed by evaporation until the volume is reduced by a half, and the precipitate is collected by filtration, dried, washed with warm water at 70° C. and finally dried. Produced is compound No. 34 in Table 1 following.

EXAMPLE 2 a)

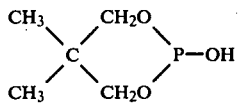
(2a)

For the preparation of the compound of formula (2a) above, the method described in Houben Weyl, Methoden der organischen Chemie, 4th edition, Volume 12/II, page 26, is used.

b)

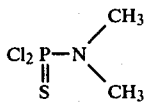
(2b)

The compound of formula (2b) above is produced according to the method of A. Michaelis, described in Annalen der Chemie, Volume 326, page 210 (1903).

(c)

27.5 Parts of the compound of formula (2a) are dissolved in 90 parts of pyridine in a stirring vessel. Into the well stirred solution under an atmosphere of nitrogen, 5.8 parts of sulphur powder are introduced at room temperature. The temperature rises to 45°-50° C. on the addition, and cooling with ice-water is used to prevent the temperature exceeding 50° C. Thereafter the cooling is maintained until the temperature of the reaction mixture has dropped to about 30° C.

13.4 Parts of the compound of formula (2b) are added dropwise to the mixture over a period of 30 minutes, and the reaction mixture is heated to 50° C. and stirred at this temperature for 4 hours. Subsequently the mixture is allowed to cool to room temperature and 80 parts of ethanol are added with stirring. The mixture is cooled to 5° C. and filtered, and the filtrate is washed with ethanol, dried and recrystallised from 200 parts of toluene to effect further purification. 20 parts of the compound No. 42 in Table 1 following are obtained.

In an analogous manner to that described in the above Example the compounds in Table 1 following are produced.

EXAMPLE 3

To 200 parts of a cellulose solution based on xanthate, which solution contains 18 parts of α-cellulose, are added with stirring 15.7 parts of a 23% aqueous dispersion of the compound No. 1 of Table 1. The dispersion is produced in the following way:

40 parts of the compound No. 1, 10 parts of a dispersing agent based on sodium naphthalene sulphonate and 110 parts of water are ground with sand in the presence of 160 parts of quarzite beads for 4 hours. The grinding is effected with ice-cooling at 1500 revolutions per minute of the grinder. After removal of the quarzite beads by filtration 140 parts of a disperstion containing 23% of the active ingredient are obtained.

A cellulose solution containing the active ingredient is extruded through spinerettes according to the conventional procedure into a precipitation bath containing per liter 125 g of sulphuric acid, 240 g of anhydrous sodium sulphate and 12 g anhydrous zinc sulphate. The fibres produced are thoroughly washed and formed into knitted products. According to the method of Fenimore and Martin (see Modern Plastics, November 1966) the knitted products are tested for flameproofing properties by measurement of the Limiting Oxygen Index (LOI).

In an analogous manner the compounds, Nos. 2, 4, 12, 15, 33 to 36 and 41 to 44 are tested and are found to possess notable flameproofing properties.

EXAMPLE 4

To 200 parts of a cellulose solution based on xanthate, which solution contains 18 parts of α-cellulose, are added 3.6 parts of the compound No. 9 of Table 1 with stirring. The production and testing of the resulting flameproofed cellulose are effected in analogous manner to that described in the previous Example. The compounds Nos. 8, 10, 14, 17 to 19 and 22 of Table 1 are tested in analogous manner and found to possess notable flameproofing properties.

EXAMPLE 5

To 200 parts of a cellulose solution based on xanthate, which solution contains 18 parts of α-cellulose, are added in succession, 1.8 parts of the compound No. 9 of Table 1 and 9 parts of a 20% aqueous dispersion of 2,4-dianilino-2,4-dioxo-1,3-diphenylcyclodiphosphazane with stirring. The production and testing of the resulting flameproofed cellulose are effected in an analogous manner to that described in Example 3.

The remaining compounds of Table 1 are also found to possess notable flameproofing properties.

Table 1

| No. | Structure | M.P. °C. |
|---|---|---|
| 1 | [Ph-NH]₂-P(=O)-O-P(=O)-[NH-Ph]₂ | 218–9 |
| 2 | [(2-CH₃-C₆H₄)-NH]₂-P(=O)-O-P(=O)-[NH-(2-CH₃-C₆H₄)]₂ | 215–6 |
| 3 | [(4-Cl-C₆H₄)-NH]₂-P(=O)-O-P(=O)-[NH-(4-Cl-C₆H₄)]₂ | 221–3 |
| 4 | [(4-CH₃-C₆H₄)-NH]₂-P(=O)-O-P(=O)-[NH-(4-CH₃-C₆H₄)]₂ | 219–220 |
| 5 | [Ph-CH₂-NH]₂-P(=O)-O-P(=O)-[NH-CH₂-Ph]₂ | 93–4 |
| 6 | [Cyclohexyl-NH]₂-P(=O)-O-P(=O)-[NH-Cyclohexyl]₂ | 210–213 |
| 7 | [Ph-N(CH₃)]₂-P(=O)-O-P(=S)(OCH₂)₂C(CH₃)₂ | 108–9 |
| 8 | (n-C₃H₇O)₂-P(=S)-O-P(=S)(OCH₂)₂C(CH₃)₂ | Oil |
| 9 | (n-C₃H₇O)₂-P(=S)-O-P(=S)-(OC₃H₇-n)₂ | Oil |
| 10 | (i-C₃H₇O)₂-P(=S)-O-P(=S)-(OC₃H₇-i)₂ | Oil |
| 11 | [Cyclohexyl-O]₂-P(=S)-O-P(=S)-[O-Cyclohexyl]₂ | Oil |
| 12 | [Ph-O]₂-P(=S)-O-P(=S)(OCH₂)₂C(CH₃)₂ | 105 |

Table 1-continued

| No. | Structure | M.P. °C |
|-----|-----------|---------|
| 13 | $\left[\left(\text{C}_6\text{H}_5\text{O}\right)_2\text{P}(=\text{S})-\text{O}-\text{P}(=\text{S})\left(\text{O}-\text{C}_6\text{H}_5\right)_2\right]$ | Oil |
| 14 | $\left[\left(\text{ClCH}_2\right)_2\text{CHO}\right]_2\text{P}(=\text{S})-\text{O}-\text{P}(=\text{S})\left[\text{OCH}(\text{CH}_2\text{Cl})_2\right]_2$ | Oil |
| 15 | $\left[\left(\text{CH}_3\right)_2\text{N}\right]_2\text{P}(=\text{S})-\text{O}-\text{P}(=\text{S})\left[\text{N}(\text{CH}_3)_2\right]_2$ | 102–103 |
| 16 | $(\text{C}_2\text{H}_5\text{O})_2\text{P}(=\text{S})-\text{O}-\text{P}(=\text{S})(\text{OC}_2\text{H}_5)_2$ | 102–8 Boiling pt. (0.3–0.5 mm of Hg) |
| 17 | $(n\text{-C}_4\text{H}_9\text{O})_2\text{P}(=\text{S})-\text{O}-\text{P}(=\text{S})(\text{OC}_4\text{H}_9\text{-}n)_2$ | Oil |
| 18 | $(i\text{-C}_4\text{H}_9\text{O})_2\text{P}(=\text{S})-\text{O}-\text{P}(=\text{S})(\text{OC}_4\text{H}_9\text{-}i)_2$ | Oil |
| 19 | $(\text{sec.C}_4\text{H}_9\text{O})_2\text{P}(=\text{S})-\text{O}-\text{P}(=\text{S})(\text{OC}_4\text{H}_9\text{-Sec.})_2$ | Oil |
| 20 | $(n\text{-C}_6\text{H}_{13}\text{O})_2\text{P}(=\text{S})-\text{O}-\text{P}(=\text{S})(\text{OC}_6\text{H}_{13}\text{-}n)_2$ | Oil |
| 21 | $\left[\left(4\text{-CH}_3\text{-C}_6\text{H}_4\text{O}\right)_2\text{P}(=\text{S})-\text{O}-\text{P}(=\text{S})\left(\text{O-C}_6\text{H}_4\text{-CH}_3\right)_2\right]$ | Oil |
| 22 | $\text{(CH}_3)_2\text{C}(\text{CH}_2\text{O})_2\text{P}(=\text{S})-\text{O}-\text{P}(=\text{S})(\text{OC}_2\text{H}_5)_2$ | Oil |
| 23 | $\text{(CH}_3)_2\text{C}(\text{CH}_2\text{O})_2\text{P}(=\text{S})-\text{O}-\text{P}(=\text{S})(\text{OC}_4\text{H}_9\text{-}n)_2$ | Oil |
| 24 | $\text{(BrCH}_2)_2\text{C}(\text{CH}_2\text{O})_2\text{P}(=\text{S})-\text{O}-\text{P}(=\text{S})(\text{OC}_3\text{H}_7\text{-}n)_2$ | Oil |
| 25 | $\text{(CH}_3)_2\text{C}(\text{CH}_2\text{O})_2\text{P}(=\text{S})-\text{O}-\text{P}(=\text{S})[\text{N}(\text{CH}_3)_2]_2$ | Oil |
| 26 | $(\text{C}_2\text{H}_5\text{O})[(\text{CH}_3)_2\text{N}]\text{P}(=\text{S})-\text{O}-\text{P}(=\text{S})(\text{OC}_2\text{H}_5)[\text{N}(\text{CH}_3)_2]$ | Oil |

Table 1-continued

| No. | Structure | M.P. °C. |
|-----|-----------|----------|
| 27 | (PhO)(─)(Me₂N)P(=S)─O─P(=S)(NMe₂)(OPh) | 130–131.5 |
| 28 | (n-C₃H₇O)(Me₂N)P(=S)─O─P(=S)(NMe₂)(OC₃H₇-n) | Oil |
| 29 | (n-C₃H₇O)(Et₂N)P(=S)─O─P(=S)(NEt₂)(OC₃H₇-n) | Oil |
| 30 | (i-C₃H₇O)(Me₂N)P(=S)─O─P(=S)(NMe₂)(OC₃H₇-i) | Oil |
| 31 | {(PhO)─}₂P(=S)─S─P(=S){─(OPh)}₂ | 131–2 |
| 32 | (n-C₃H₇O─)₂P(=S)─S─P(=S)(─OC₃H₇-n)₂ | Oil |
| 33 | [CH₃,CH₃]C(CH₂O)₂P(=S)─S─P(=S)(OCH₂)₂C[CH₃,CH₃] | 235–6 |
| 34 | [BrCH₂,BrCH₂]C(CH₂O)₂P(=S)─S─P(=S)(OCH₂)₂C[CH₂Br,CH₂Br] | 164–165.5 |
| 35 | {[CH₃,CH₃]C(CH₂O)₂P(=S)─O─P(=O)(NMe₂)}₂ | 128–9 |
| 36 | {[CH₃,CH₃]C(CH₂O)₂P(=S)─O─P(=O)(N-piperidino)}₂ | 160–2 |
| 37 | {[CH₃,CH₃]C(CH₂O)₂P(=S)─O─P(=O)(N(CH₃)Ph)}₂ | 144–5 |
| 38 | {[BrCH₂,BrCH₂]C(CH₂O)₂P(=S)─O─P(=O)(N(C₃H₇-n)₂)}₂ | 127–9 |

Table 1-continued

| No. | Structure | M.P. °C. |
|---|---|---|
| 39 | ![structure 39] | 118-9 |
| 40 | ![structure 40] | Oil |
| 41 | ![structure 41] | 159-60 |
| 42 | ![structure 42] | 158-9 |
| 43 | ![structure 43] | 118-9 |
| 44 | ![structure 44] | 144-5 |
| 45 | ![structure 45] | 105-6 |
| 46 | ![structure 46] | 157-8 |

What is claimed is:

1. As a flameproofing composition for regenerated cellulose, a fine dispersion of a flameproofing agent in water, said flameproofing agent being a compound of the formula,

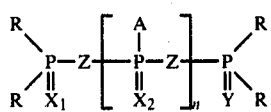

in which each R, independently, is a radical $-OR_1$ (a) or

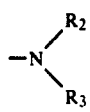

or two moieties R bound to the same phosphorus atom form a radical (c),

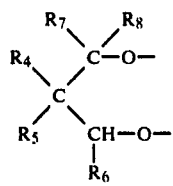

and each of the other two moieties R, independently, is a radical (a) or (b), or the other two moieties R bound to the same phosphorus atom form a second radical (c), independent from the first radical (c);

each of $X_1$, $X_2$, Y and Z, independently, is oxygen or sulphur;

n is zero or 1;

A is a radical (a) or

 (d);

each $R_1$, independently, is methyl; ethyl or propenyl, each unsubstituted or substituted by 1 to 3 halo substituents or by a ($C_{1-6}$) alkoxy group; ($C_{3-12}$) alkyl or ($C_{4-12}$) alkenyl, each unsubstituted or substituted by 1 to 4 halo substituents; ($C_{5-8}$) cycloalkyl or ($C_{5-8}$) cycloalkyl ($C_{1-4}$) alkyl containing a total of 7 to 9 carbon atoms, each unsubstituted or substituted by 1 or 2 halo substituents; phenyl, unsubstituted or substituted by 1 to 5 halo substituents or by 1 to 3 substituents selected from ($C_{1-3}$) alkyl and ($C_{1-3}$) alkoxy; or phenyl ($C_{1-4}$) alkyl, unsubstituted or substituted aromatically by 1 to 5 halo substituents or by 1 to 3 substituents selected from ($C_{1-3}$) alkyl and ($C_{1-3}$) alkoxy;

each $R_2$, independently, is ($C_{1-4}$) alkyl; cyclohexyl; benzyl; or phenyl, unsubstituted or substituted by 1 or 2 chloro substituents of which only one can occupy or ortho-position, by a bromo substituent in the para-position, or by 1 or 2 substituents selected from ($C_{1-3}$) alkyl and ($C_{1-3}$) alkoxy, the aggregate of the carbon atoms thereof not exceeding 3;

each $R_3$, independently, is ($C_{1-4}$) alkyl or hydrogen; or any $R_2$ and $R_3$, independently, together with the nitrogen atom to which they are bound, form a 5- or 6-membered, saturated heterocyclic ring which may contain as a ring member an oxygen or sulphur atom, or a second nitrogen atom to which is bound a ($C_{1-4}$) alkyl group;

each $R_4$ and $R_5$, independently, is hydrogen; ($C_{1-4}$) alkyl; $CH_2Cl$; $CH_2Br$ or phenyl;

or any $R_4$ and $R_5$, independently, together with the carbon atom to which they are bound, form a cyclohexylidene, cyclohexenylidene or 3,4-dibromocyclohexylidene ring;

each $R_6$ and $R_8$, independently, is hydrogen or ($C_{1-4}$) alkyl;

each $R_7$, independently, is hydrogen or methyl, $R_9$ is methyl; ethyl, unsubstituted or substituted by a halo substituent; propyl, unsubstituted or substituted by 1 or 2 halo substituents; ($C_{4-12}$) alkyl, unsubstituted or substituted by 1 to 3 halo substituents; cyclohexyl; benzyl; or phenyl, unsubstituted or substituted by 1 or 2 substituents selected from ($C_{1-3}$) alkyl and ($C_{1-3}$) alkoxy, the aggregate of the carbon atoms thereof not exceeding 3, by 1 or 2 chloro substituents, by 1 or 2 chloro substituents and by 1 or 2 substituents selected from ($C_{1-3}$) alkyl and ($C_{1-3}$) alkoxy, the aggregate of the carbon atoms thereof not exceeding 3, by a bromo substituent in the para-position or by a bromo substituent in the para-position and by 1 or 2 substituents selected from ($C_{1-3}$) alkyl and ($C_{1-3}$) alkoxy, the aggregate of the carbon atoms thereof not exceeding 3;

$R_{10}$ is hydrogen; methyl; ethyl, unsubstituted or substituted by a halo substituent; propyl, unsubstituted or substituted by 1 or 2 halo substituents; ($C_{4-12}$) alkyl, unsubstituted or substituted by 1 to 3 halo substituents; cyclohexyl; benzyl or phenyl;

or $R_9$ and $R_{10}$, together with the nitrogen atom to which they are bound, form a 5- or 6-membered, saturated heterocyclic ring which may contain as a ring member an oxygen or sulphur atom, or a second nitrogen atom, to which is bound a ($C_{1-4}$) alkyl group, with the provisos that:
(i) when one or more of $X_1$, $X_2$ and Y is oxygen, then Z can only be oxygen,
(ii) when $X_1$ and Y are both oxygen, then only up to 2 of the moieties R can be a radical (a),
(iii) when there are more than 2 radicals (a) in the molecule, only up to 2 of them can be methoxy,
(iv) when Z is oxygen and n is zero, only one radical (c) can be present in the molecule,
(v) when $X_1$ or Y is oxygen, then $R_2$ in any radical (b) attached to that same phosphorus atom as the oxygen atom is other than alkyl,
(vi) when two radicals (b) are attached to a phosphorus atom and $X_1$ or Y attached to that same phosphorus atom is sulphur, then both of the moieties $R_2$ in these radicals (b) are ($C_{1-4}$) alkyl,
(vii) when n is 1, or when n is zero and $R_2$ in any radical (b) is ($C_{1-4}$) alkyl, any $R_3$, or $R_3$ in that same radical (b), respectively, is other than hydrogen,
(viii) at least one of $R_4$, $R_5$, $R_6$, $R_7$ and $R_8$ in any radical (c) is other than hydrogen,
(ix) when each of $R_4$ and $R_5$, independently, in any radical (c) is $CH_2Cl$ or $CH_2Br$ or both $R_4$ and $R_5$, together with the carbon atom to which they are bound form one of the rings indicated above, each of $R_6$, $R_7$ and $R_8$ in the same radical (c) is hydrogen,
and (x) when each of $X_1$ and Y is oxygen, each of $R_4$ and $R_5$, independently, in any radical (c) is $CH_2Cl$ or $CH_2Br$ or both $R_4$ and $R_5$, together with the carbon atom to which they are bound, form one of the rings indicated above.

2. A dispersion according to claim 1 wherein the flameproofing agent is a compound of the formula

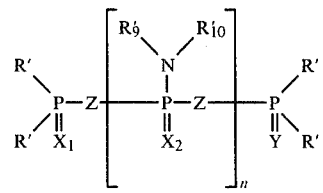

in which each R', independently, is a radical $-OR_1'$ (a') or

or two moieties R' bound to the same phosphorus atom form a radical (c')

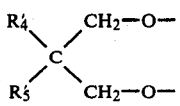

and each of the other two moieties R', independently, is a radical (a') or (b'), or the other two moieties R' bound to the same phosphorus atom form a second radical (c'), independent from the first radical (c'), each of $X_1$, $X_2$, Y and Z, independently, is oxygen or sulphur, n is zero or 1, each $R_1'$, independently, is ethyl, unsubstituted or substituted by a halo substituent; ($C_{3-6}$) alkyl, unsubstituted or substituted by 1 to 3 halo substituents; ($C_{3-6}$) alkenyl, unsubstituted or substituted by 1 or 2 halo substituents; cyclohexyl; phenyl, unsubstituted or substituted by 1 to 3 chloro substituents, by a bromo substituent in the para-position or by 1 to 3 methyl substituents; or benzyl, unsubstituted or substituted by 1 to 3 chloro substituents or by a bromo substituent in the para-position;

each $R_2'$, independently, is ($C_{1-3}$) alkyl; or phenyl, unsubstituted or substituted by a chloro substituent, by a bromo substituent in the para-position or by a methyl substituent;

each $R_3'$, independently, is ($C_{1-3}$) alkyl or hydrogen;

each $R_4'$ and $R_5'$, independently, is ($C_{1-4}$) alkyl; $CH_2Cl$ or $CH_2Br$;

or any $R_4'$ and $R_5'$, independently, together with the carbon atom to which they are bound, form a cyclohexylidene, cyclohexenylidene or 3,4-dibromocyclohexylidene ring;

$R_9'$ is ($C_{1-4}$) alkyl; cyclohexyl; benzyl or phenyl;

$R_{10}'$ is hydrogen; ($C_{1-4}$) alkyl; cyclohexyl; benzyl or phenyl;

or $R_9'$ and $R_{10}'$, together with the nitrogen atom to which they are bound, form a piperidino or morpholino ring, with the provisos that:

(i) when one or more of $X_1$, $X_2$ and Y is oxygen, then Z can only be oxygen, (ii) when $X_1$ and Y are both oxygen, then each moiety R', independently, is a radical (b'), (iii) when Z is oxygen and n is zero, only one radical (c') can be present in the molecule, (iv) when $X_1$ or Y is oxygen, then $R_2'$ in any radical (b') bound to that same phosphorus atom is other than alkyl, (v) when two radicals (b') are attached to a phosphorus atom, and $X_1$ and Y attached to that same phosphorus atom is sulphur, then both of the moieties $R_2$ in these radicals (b') are ($C_{1-3}$) alkyl, (vi) when one of the moieties $R_2'$ and $R_3'$ bound to the same nitrogen atom in a radical (b') is ethyl or propyl, the other must be ethyl or propyl, (vii) when n is 1, or when n is zero and $R_2'$ in any radical (b') is ($C_{1-3}$) alkyl, any $R_3'$, or $R_3'$ in that same radical (b'), respectively, is other than hydrogen, and (viii) when each of $X_1$ and Y is oxygen, each of $R_4'$ and $R_5'$, independently, in any radical (c') is $CH_2Cl$ or $CH_2Br$ or both $R_4'$ and $R_5'$, together with the carbon atom to which they are bound form one of the rings indicated above.

3. A dispersion according to claim 2 wherein the flameproofing agent is a compound of the formula

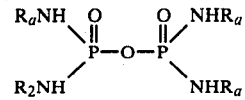

in which $R_a$ is phenyl, unsubstituted or substituted by a chloro substituent in the para-position or by a methyl substituent.

4. A dispersion according to claim 2 wherein the flameproofing agent is a compound of the formula

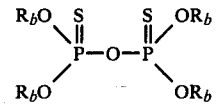

in which each $R_b$, independently, is n-propyl or isopropyl, each unsubstituted or substituted by 1 or 2 halo substituents; ($C_{4-6}$) alkyl, unsubstituted or substituted by 1 to 3 halo substituents; cyclohexyl; or phenyl, unsubstituted or substituted by a methyl substituent; or two moieties $R_b$ bound via oxygen atoms to the same phosphorus atom form a radical (c''),

wherein each $R_4''$ and $R_5''$, independently, is ($C_{1-3}$) alkyl; $CH_2Cl$ or $CH_2Br$, with the proviso that when $R_4''$ is $CH_2Br$, $R_5''$ is other than $CH_2Cl$, and when $R_5''$ is $CH_2Br$, $R_4''$ is other than $CH_2Cl$, with the proviso that no more than one radical (c'') is present in the molecule.

5. A dispersion according to claim 2 wherein the flameproofing agent is a compound of the formula

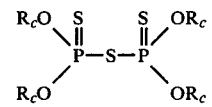

in which $R_c$ is propyl or butyl, or two moieties $R_c$ bound via oxygen atoms to the same phosphorus atom form a radical (c'')

wherein each $R_4''$ and $R_5''$, independently, is ($C_{1-3}$) alkyl; $CH_2Cl$ or $CH_2Br$, with the proviso that when $R_4''$ is $CH_2Br$, $R_5''$ is other than $CH_2Cl$, and when $R_5''$ is $CH_2Br$, $R_4''$ is other than $CH_2Cl$.

6. A dispersion according to claim 2 wherein the flameproofing agent is a compound of the formula

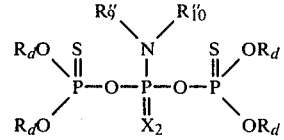

in which $R_d$ is n-propyl or isopropyl, each unsubstituted or substituted by 1 or 2 halo substituents; ($C_{4-6}$) alkyl; or two moieties $R_d$ bound via oxygen atoms to the same phosphorus atom form a radical (c''),

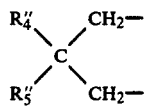

wherein each $R_4''$ and $R_5''$, independently, is ($C_{1-3}$) alkyl; $CH_2Cl$ or $CH_2Br$, with the proviso that when $R_4''$ is $CH_2Br$, $R_5''$ is other than $CH_2Cl$, and when $R_5''$ is $CH_2Br$, $R_4''$ is other than $CH_2Cl$;

$X_2$ is oxygen or sulphur;

$R_9''$ is ($C_{1-4}$) alkyl; cylclohexyl or benzyl; and $R_{10}''$ is hydrogen or ($C_{1-4}$) alkyl;

or $R_9''$ and $R_{10}''$, together with the nitrogen atom to which they are bound, form a piperidino or morpholino ring.

7. A dispersion according to claim 1 which, in addition to the flameproofing agent, contains: (a) at least one dispersion stabilizer and at least one dispersing agent; or (b) at least one dispersion stabilizer or at least one dispersion agent.

8. A dispersion according to claim 7 which, in addition to the flameproofing agent, contains at least one dispersion stabilizer or at least one dispersion agent.

9. A dispersion according to claim 8 which, in addition to the flameproofing agent, contains at least one dispersion agent.

10. A dispersion according to claim 9 in which the dispersion agent is sodium naphthalene sulphonate.

* * * * *

UNITED STATES PATENT AND TRADEMARK OFFICE
CERTIFICATE OF CORRECTION

PATENT NO. : 4,154,691
DATED : May 15, 1979
INVENTOR(S) : Claudine Mauric/Rainer Wolf It is certified that error appears in the above–identified patent and that said Letters Patent are hereby corrected as shown below:

First Page, please insert

-- Foreign Application Priority Data

| May 30, 1975 | Switzerland | 6992/75 |
| August 22, 1975 | Switzerland | 10908/75 |
| Nov. 5, 1975 | Switzerland | 14262/75 |
| Nov. 18, 1975 | Switzerland | 14918/75 |
| Nov. 27, 1975 | Switzerland | 15387/75 --. |

Claim 1, Col. 21, in the definition of $R_2$, line 4; change "or" to --an--.

Claim 3, Col. 24; delete the formula

"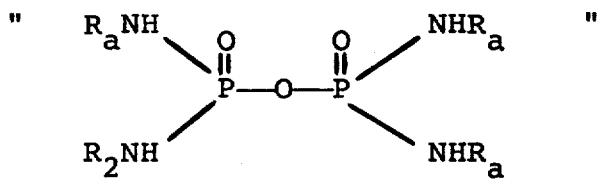"

and substitute therefor

UNITED STATES PATENT AND TRADEMARK OFFICE
CERTIFICATE OF CORRECTION

PATENT NO. : 4,154,691
DATED : May 15, 1979
INVENTOR(S) : Claudine Mauric/Rainer Wolf It is certified that error appears in the above—identified patent and that said Letters Patent is hereby corrected as shown below:

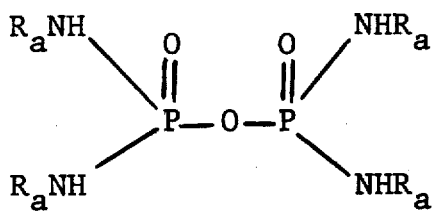

Signed and Sealed this

Eighteenth Day of March 1980

[SEAL]

Attest:

Attesting Officer

SIDNEY A. DIAMOND

Commissioner of Patents and Trademarks